(12) United States Patent
Gedeon et al.

(10) Patent No.: US 7,405,006 B2
(45) Date of Patent: Jul. 29, 2008

(54) METHOD OF TREATING SURFACES FOR SELF-STERILIZATION AND MICROBIAL GROWTH RESISTANCE

(76) Inventors: Anthony Alan Gedeon, 10 Crossleaf Ct. West, Palm Coast, FL (US) 32137; Andrew Greig, 926 S. 17th St., Arlington, VA (US) 22202

( * ) Notice: Subject to any disclaimer, the term of this patent is extended or adjusted under 35 U.S.C. 154(b) by 334 days.

(21) Appl. No.: 11/013,686

(22) Filed: Dec. 16, 2004

(65) Prior Publication Data

US 2005/0249955 A1    Nov. 10, 2005

Related U.S. Application Data

(60) Provisional application No. 60/530,017, filed on Dec. 16, 2003.

(51) Int. Cl.
*B32B 25/20*    (2006.01)

(52) U.S. Cl. ........................ 428/447; 427/387

(58) Field of Classification Search ................. 428/447; 427/387
See application file for complete search history.

(56) References Cited

U.S. PATENT DOCUMENTS

| | | | |
|---|---|---|---|
| 3,944,702 A | 3/1976 | Clark | |
| 3,976,497 A | 8/1976 | Clark | |
| 3,986,997 A | 10/1976 | Clark | |
| 4,027,073 A | 5/1977 | Clark | |
| 5,929,159 A | 7/1999 | Schutt et al. | |
| 6,361,871 B1 | 3/2002 | Jenkner et al. | |
| 6,384,119 B1 | 5/2002 | Tye et al. | |
| 6,395,856 B1 | 5/2002 | Petty et al. | |
| 6,432,191 B2 | 8/2002 | Schutt | |
| 6,451,382 B2 | 9/2002 | Schutt et al. | |
| 6,469,120 B1 | 10/2002 | Elfersy et al. | |
| 2001/0056141 A1 | 12/2001 | Schutt | |
| 2002/0102417 A1 | 8/2002 | Schutt et al. | |
| 2003/0219562 A1 | 11/2003 | Rypacek et al. | |
| 2005/0008763 A1* | 1/2005 | Schachter | .................. 427/2.24 |

OTHER PUBLICATIONS

N. Andrew Greig; A Brief Overview of Reactive Silanes and Other Siloxane Coatings as Corrosion-Preventive Surface Modification Treatments, Jun. 2002.

* cited by examiner

*Primary Examiner*—Kuo-Liang Peng
(74) *Attorney, Agent, or Firm*—Charles J. Prescott

(57) ABSTRACT

Coating composition, articles, and methods for applying reactive silanol coating compositions having electron deficient surfaces formed as the coating composition cures wherein organic radical groups from the silanes are forced to the surface of the coating. The silicon atoms in the interpenetrating silicon-oxygen structure below retain electrons skewing the electron cloud downward creating an electron deficient or net positively charged surface. The resultant surface exhibits self-sterilization without toxic biocide additives due to the electron deficient surface. The surface is also extremely tight and thereby absent nutrients for microorganisms, discouraging organic growth such as mold. This unique positively charged surface further exhibits both hydrophobic and oleophobic qualities providing ease of cleaning for maintenance, particularly for hospital beds, equipment, floors, walls, curtains, bathrooms, or all the surfaces inside and outside of an ambulance and the equipment contained therein. Similarly, buildings and their contents, construction materials, and infrastructure can be made self-decontaminating and greatly simplify cleaning from potential bio-warfare agents.

26 Claims, No Drawings

METHOD OF TREATING SURFACES FOR SELF-STERILIZATION AND MICROBIAL GROWTH RESISTANCE

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

1. Field of the Invention

This invention relates generally to surface treatments for sterilization, cleanliness and microbial growth reduction and more particularly to a method of treating surfaces with reactive silanol which become self-sterilizing and which resist microbial growth without the use of biocides, and for the production of articles exhibiting microbial-resistant surface properties.

2. Description of Related Art

Siloxane coatings applied as reactive silanols have been granted three US patents known to applicants: Schutt/Gedeon, U.S. Pat. No. 5,929,159, Oligomeric silicon coating compositions, articles coated therewith and method for forming coating composition and coated articles based thereon; Schutt, U.S. Pat. No. 6,432,191, Silane-based, coating compositions, coated articles obtained there from and methods of using same and Schutt/Gedeon/Stanich, U.S. Pat. No. 6,451,382, Method for improving heat efficiency using silane coatings and coated articles produced thereby the entire disclosures of which are incorporated herein, in their entireties, by reference thereto.

The content of matter formulas described in these patents and any current or future derivative formulas for reactive silanols where such materials are applied using the methods defined herein for the purposes claimed herein are incorporated by reference. While not wishing to be bound by the following formulae provided for information, examples of reactive silanol compositions as described in the referenced Schutt et. al. patents are any coating, polish, primer, penetrant, sealer, or surface modification treatment comprised of an aqueous or non-aqueous dispersion of the partial condensate of monomethyl or monethyl silanol (by hydrolysis of monomethyl or monethyl alkoxysilane) alone or in admixture with minor amounts of other silanols, e.g., gamma-glycidyloxy silanol, phenyl silanol, etc, wherein the dispersions contain divalent metal cations, e.g., $Ca^{+2}$, alcohol or water dispersants, and which may optionally contain film-enhancing additives such as, but not limited to, hydrolysis catalysts like acetic acid, ethylene glycol ether co-solvents, silicates or hydrolyzed silicates, solid or water-soluble pigments, gellation inhibitors like chromium acetate hydroxides, or metal alcholates of the of formula (2):

$$M(OR^3)_m \quad (2)$$

where M is a metal valence 2, 3 or 4, or mixture of two or more such metals;

R represents a lower alkyl group; and, m represents a number or 2, 3 or 4;

or any reactive silanol pre-catalyzed (hydrolyzed) by adding water and additives to silanes and inducted for at least five, but not more than 20 minutes, and then diluted with solvent such as, but not limited to, lower alkanols such as isopropyl and ethyl alcohol to inhibit further polycondensation and cross-linking so as to be subsequently applied as 1-part reactive silanol that can be applied to a surface by spraying, brushing, or wiping; and which then optionally can be cross-linked into a polysolixane film by applying water and, preferably, water acidified with acetic acid or a mineral acid such as boric acid or other condensation additive where that water or aqueous mixture is mechanically buffed into the silanol layer using a wiping cloth, preferably, a microfiber polishing cloth or mechanical buffing wheel or similar device.

Silicon-based or silicon-containing coatings and penetrants that can be applied and cured at ambient temperatures include silanes (typically alkylalkoxysilanes or alkyltrialkoxysilanes), siloxanes (typically oligomerous alkylalkoxysiloxanes or silsesquioxanes), silicates (including ethyl silicates, sodium silicates, and potassium silicates), methyl siliconates, blends of the above, and hybrid organic-inorganic paints and coatings including silicone alkyds, epoxy-siloxane coatings and acylic-siloxane coatings. In a recent symposium, a good history of recent developments was given by N. Andrew Greig of Arlington, Va.; "A Brief Overview of Reactive Silanes and other Siloxane Coatings as Corrosion Preventatives".

In the early 1970s, Harold A. Clark of Dow Corning Corporation patented a variety of siloxane systems for lens coatings, fire-retardant binders for fire insulation, and a new variety of paints (see U.S. Pat. Nos. 3,944,702, 3,976,497, and related patents). Clark's invention involved generating $RSi(OH)_3$ silanols in situ by adding trialkoxysilanes in an isopropyl alcohol-water carrier to an acidic dispersion of colloidal silica (Arkles, 607). This resulting sol condenses into a siloxanol polymer gel forming Si—O—Si chains that further cures to form a hard, adherent layer of silsesquioxanes ($RsiO_{2/3}$). Clark created paint coatings by adding a variety of pigments to form flame-resistant paints and high-gloss enamels, to name a few.

When the Clark patents from 1976 expired, Dr. John Schutt of NASA Goddard and Tony Gedeon developed a new siloxane approach to overcome a weakness in the original Dow patents. Specifically, their U.S. Pat. No. 5,929,159 in July 1999 claimed that use of colloidal silica, "especially when used in or near the amounts contemplated by the above Dow Corning (Clark) patents, renders the coatings porous or microporous and drastically reduces the corrosion resistance of the coatings." Their approach was to replace colloidal silica with divalent cations, particularly, $Ca^{+2}$.

Again quoting from the '159 patent:

"Generally, when the silicon atom is both trifunctionally and quadrifunctionally hydroxylated, the resulting siloxane network accommodates minimally the passage of water vapor and in some circumstances also the passage of water as well as oxygen. Because of this property, bonding resulting from the hydroxylation at a metallic interface is incomplete and corrosion can occur. The present coating compositions better utilize the reactivity of the silanol moiety with substrate oxy and hydroxy species and promote the formation of a contiguous interfacial layer unaffected by surface and bulk diffusion of water, water vapor and oxygen. This is accomplished, at least in part, by replacing all or most of the colloidal silica in formulations of the type described in the Dow Corning (Clark) patents mentioned above with divalent metal ($M^{+2}$) ions, such as, for example, $Cu^{+2}$, $Zn^{+2}$, $Ca^{+2}$ $Co^{+2}$, and $Mn^{+2}$.

Other objectives of the new coating cited in this '159 patent include:

- to provide abrasion resistant coating compositions suitable for metallic and non-metallic surfaces.
- to provide transparent, glass-like abrasion-resistant and corrosion resistant coating compositions as well as coated articles.
- to provide such improved coating compositions as aqueous formulations with acceptable volatile organic component (VOC) levels and, therefore, environmentally acceptable.
- to provide such coating compositions which may be prepared easily and economically and are easy to apply to various types of substrates.
- to develop a coating composition suitable for coating marine surfaces, such as aluminum boat hulls, to render the surfaces corrosion resistant in a salt water environment.

The resultant condensed organic-inorganic hybrid layer is thin (5μ-1 mil), transparent, and hard (pencil hardness 11H). Because the molecular size of the silanols before they cure into siloxane oligomers is so small, the sol penetrates pores in the substrate to achieve better sealing and bonding. The substrate can be a metal, non-metal, or an organic coating.

U.S. Pat. No. 6,451,382 to Schutt, Gedeon, and Stanich identifies that cured siloxane coatings inhibit molds, fungus, and bacteria by being hydrophobic and absent nutrients to support organic growth, and discloses that thin siloxane coatings are preferred for enhancing heat transfer, but does not link an observed antimicrobial effect to the nature of the film formed.

U.S. Pat. No. 5,954,869 notes that the antimicrobial properties of commercially available organosilanes such as the antimicrobial Dow Corning 5700 (Dow Corning Corporation, Midland, Mich.) are well known, but are impractical because of the instability of such compounds due to undesirable self-hydrolyzation. That is, such compounds are unstable in water. It further notes that quaternary ammonium silicon compounds also have been employed to sterilize or disinfect many surfaces, but that their employment is still limited because of their toxicity often as a result of the solvent system used to deliver the compound, the necessity for a solvent solution (for instance, Dow Corning antimicrobial agents contain 50% methanol), short term stability (stability of aqueous silane solutions varies from hours to several weeks only) and poor water solubility.

The present invention recognizes the discovery that, as oligomeric siloxane coatings polymerize from linear reactive polysilanols, the silicon atoms rotate to allow the larger organic groups upward mobility to the surface of the coating. Although not wishing to be bound by any theory of operation, this physical structure creates a permanently electron-deficient surface that inhibits growth of bacteria, molds, fungus, and algae, that inhibits proteins that some bacteria elaborate in order to attach to a surface and thrive, and may be responsible for killing microorganisms. A simplified model of the cured structure is provided.

This patent discloses water-stabilized organosilane compounds formed by mixing an organosilane, optionally having a nonhydrolyzable organic group, but having one or more hydrolyzable groups, with a polyol containing at least two hydroxy groups such as a carbohydrate, wherein at least any two of the hydroxy groups are separated by no more than two intervening atoms and methods for using the same to treat surfaces and articles by contacting a substrate with the product.

The present invention overcomes the limitations of these and other silicon-based antimicrobial treatments. The reactive silanols as cited herein are stable by being packaged in separate containers for mixing and hydrolyzation when needed for coating or by having a partially catalyzed silanol cured by post-coating application of water or water and curing agent and promoting cross-linking by mechanical rubbing. Under the methods described herein, the toxic alcohol emissions can be controlled during hydrolyzation to form reactive silanols and by controlling ventilation during application. Fresh formation of linear silanols from hydrolyzing tailored blends of preferentially tri-functional organosilanes maximizes the surface bonding reaction of hydroxy moieties with substrate hydroxides and oxides.

This method of formulation and mixing of reactive silanols, combined with the surface cleaning and application methods described herein allows surface treatment by standard paint application techniques or by dipping articles into reactive silanol sols and film bonding and curing at ambient temperatures. The resulting siloxane structure is cross-linked, insoluble in water, oil, solvents, and most acids and produces a thermodynamically stable antimicrobial, antifungal surface without resorting to additives. Further, the cured siloxane neither emits gases nor leaches toxins, nor is it toxic as a solid.

BRIEF SUMMARY OF THE INVENTION

Advances in oligomeric siloxane coatings, particularly the invention of ambient temperature curing reactive silanol coatings, have arisen in the past several years that offer opportunities to solve problems that could not be addressed with traditional coating materials and methods. Although this class of coatings is normally cited for their corrosion resistance and robust environmental performance, it has now been discovered that they also can be made to exhibit the unusual phenomenon of having electron deficient surfaces. The electron deficient surface is formed as the coating cures in that organic radical groups from the silanes used in the formulation are forced to the surface of the coating. The silicon atoms in the interpenetrating silicon-oxygen structure below retain electrons skewing the electron cloud downward creating an electron deficient or net positively charged surface.

Although not wishing to be bound by any particular theory of operation, the resultant surface exhibits self sterilization without toxic biocide additives due to the electron deficient surface. The electron deficient surface disrupts the functional living processes of bacteria and viruses. Also the surface is extremely tight and is absent nutrients for microorganisms, and as a result, discourages organic growth such as mold. This unique positively charged surface further exhibits both hydrophobic and oleophobic qualities providing ease of cleaning for maintenance, sterilization, or decontamination, particularly for hospital beds, equipment, floors, walls, curtains, bathrooms, or all the surfaces inside and outside of an ambulance, police cars, and other emergency and medically related vehicles and aircraft and the equipment contained therein.

Similarly, buildings and their contents, construction materials, and infrastructure can be made self decontaminating and greatly simply cleaning from potential bio-warfare agents. Also, first responders for biothreats can be similarly protected by coating suits, equipment, vehicles and aircraft through biocidal or biostatic action that would self-sterilize or allow surfaces to be remediable. That is, treated surfaces can be made sterile or the microbe population can be reduced to below the Minimal Infection Concentration (MIC) with no cleaning, minimal cleaning with simple soap and water instead of disinfectants or harsh chemicals, or can be decontaminated with harsh chemicals or disinfectants and no scrubbing without damaging the treated surfaces.

The method of mixing (catalyzation) and application of reactive silanols of the types described in or derived from the prior art cited herein to achieve contaminant-resistant easy-clean surfaces involves the following steps:

1. Hydrolyzation of a specific alkoxysilane or a blend of alkoxysilanes with water to produce active silanol groups where R is a nonhydrolyzable organic substituent such as, but not limited to, a methyl ($CH_3$), ethyl ($C_2H_5$), propyl ($C_2H_7$), vinyl ($C_2H_3$), or phenyl ($C_6H_5$) group and where the hydrolyzable group is, but not limited to at least one and preferably three, methoxy ($OCH_3$), ethoxy ($OC_2H_5$), or chloro (Cl) group(s) as depicted in formula (3):

$$R-Si-(OCH_3)_{+3}H_2O \rightarrow R-Si-(OH)_3 + 3CH_2OH\uparrow \quad (3)$$

The water for hydrolyzation can be added as reagent-grade water, can come from the atmosphere, or be absorbed from the surface of the material being coated. Hydrolyzation releases an alcohol by-product, such as methanol or ethanol, which is released as a gas during open pot mixing. Open pot mixing is preferred to force formula (3) to the right (complete hydrolyzation) and to allow controlled release of alcohols, other solvents, or both.

2. Polycondensation to form predominantly linear oligomers of polysilanols (siloxanols)(formation of siloxane bonds) to form a reactive silanol sol per formula (4):

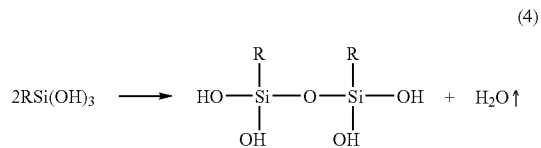

(4)

... and so on for 30-minute to 12-hour induction period.

Reactive silanol sols as applied to methods described herein typically have isopropyl alcohol (IPA), ethyl alcohol, propylene glycol ethers, or other solvents added to reduce viscosity for surface penetration and wetting, and to accelerate evaporation of water. Curing agents such as, but not limited to, tetrabutoxytitanate and wetting agents may also be added to accelerate film formation and substrate bonding. Pigments, dyes, water soluble additives such as corrosion inhibitors, and chemically bonded additives such as corrosion inhibitors may be added to produce distinctive film properties, provided the additions are not so great to disrupt the development of a low-porosity interpenetrating network of organosolixanes with organic moieties oriented toward the surface.

3 to 5. Application and Curing:

The reactive silanol sol is applied to a surface and covalently bonds with surface oxides and hydroxides to form metal oxysilicates, condenses, and cross-links into amorphous interpenetrating network of siloxanes with organic moieties oriented toward the surface of the film per formulae (5).

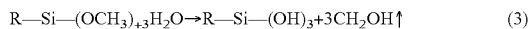

Oxidized Metal or Aged Non-metallic Substrate

| Application | Hydrogen Bonding | Bonding/Condensation |

(5)

Note that water is both a reactant (hydrolyzation) and a reaction product (polycondensation and bonding with surface oxides and hydroxides). Acetic acid, boric acid, or other acids can be used to accelerate hydrolyzation and keep the structure open long enough to allow reaction product water and solvents to escape during substrate bonding.

Another method of producing polysiloxane films with reactive silanols involves partially catalyzing silanes with water and additives and inducting for at least five, but not more than 20 minutes, and then diluting with solvent such as, but not limited to, isopropyl alcohol to inhibit further polycondensation and cross-linking so as to be subsequently applied as 1-part reactive silanol that can be applied to a surface by spraying, brushing, or wiping; and which then optionally can be cross-linked into a polysolixane film by applying water and, preferably, water acidified with acetic acid or a mineral acid such as boric acid or other condensation additive that is mechanically buffed into the silanol layer using a wiping cloth, preferably, a microfiber polishing cloth or mechanical buffing wheel or similar device.

Although not wishing to be bound by any particular theory of operation, this invention notes that the structure of the cured film, namely a thin layer of interpenetrating polysiloxane with organic moieties predominately oriented toward the surface, accounts for the unique properties afforded to substrates treated with reactive silanols and that this structure depends not only on the Schutt et. al, content-of-matter patents cited as prior art, but on the mixing and application of the reactive silanol. Specifically:

Water up to 50% of the catalyzed silane-water-additives mixture, but preferably no more that 33% of the catalyzed mixture can be added in excess of the amount stoichiometrically needed for complete hydrolyzation of precursor alkoxysilanes to control the rate of polycondensation of oligomeric silanols and to improve wetting and application viscosity;

The post-catalyzation induction time can be adjusted to allow complete hydrolyzation of all precursor silanes and to allow formation of oligomers of polysilanols, but limited so that the mixture does not gel or form excessive molecular weight polymers (100,000 atomic mass units or greater) of reactive silanols that interfere with proper film formation;

Induction times and curing times can be modified by varying the amount and types of curing agents and acids used;

The blend of added solvents can be such that formation of cyclic silanols is inhibited and may be blended to achieve longer drying times to allow for overlapping coats (called wet line control);

Solvents can be added to the inducted mixture to reduce viscosity for application and increase pot life, but too much added solvent, including water, interferes with film formation and substrate bonding described herein to achieve contamination-resistant and easy-clean surfaces.

The thin, glass-like film is clear and, unlike clear organic coatings, does not yellow, oxidize, or lose gloss. Si—O bonds are not only 130% stronger than C—C bonds found in organic coatings, but the polysiloxane structure is almost fully oxidized making it thermodynamically stable. The organic substituents are largely excluded from cross-linking reactions so tend to rotate to the surface of the film as it cures. This property of reactive silanols not only accounts for the varying surface properties that can be engineered, but explains why reactive silanols should be applied only in very thin films. If the sol is allowed to pool into thick deposits, the organic groups cannot orient to the film-air interface causing incomplete cross-linking of the film.

REFERENTIAL EXAMPLES

The invention will now be illustrated by the following non-limiting methods and articles produced thereby. It is understood that these examples are given by way of illustration only and without intent to limit the invention thereto.

I. A method for producing self sterilizing (either biocidal or bacteria-static), surfaces or articles with the additional properties of simplified cleaning of contamination and residues, and resistance to microbial growth without biocides by coating same as an overcoat to other coatings, or directly over uncoated materials or fabrics with oligomeric siloxanes, applied as catalyzed or partially catalyzed reactive silanol, to create a net positive surface charge on the coating to effect the stated properties. Preferred surfaces or articles include but are not limited to all medical, health club, transportation terminal, casino or like facility surfaces, particularly those surfaces subject to frequent touch such as floors, handrails, rest rooms, counter tops, and food service areas; equipment and medical equipment including, but not limited to keyboards, telephones, wheel chairs, ventilators, beds/gurneys, blood pressure cuffs/bulbs, slot machine handles, gaming chips, and exercise equipment, HVAC (preferably but not limited to evaporators, drip pans and condensation ducts, blowers, and supply ducts/vents), furniture, and decorative surfaces to mitigate bacterial and virus contamination; surfaces and equipment contained in ambulances, vehicles or aircraft; and self decontamination and easy cleaning of bio-warfare agents, both germ and organic compounds from buildings and their contents, HVAC, construction materials, infrastructure, and contents of buildings by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

II. A method of self-sterilization and providing a biostatic or biocidal surface that is remediable using siloxane coatings without biocides for surfaces that experience exposure to blood, bacteria, viruses, and contamination from dirt and body fluids wherein an electron deficient surface interrupts the reproduction of bacteria and viruses by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

III. A method of self-sterilization and providing a biostatic or biocidal surface that is remediable using siloxane coatings without biocides for surfaces that experience exposure to blood, bacteria, viruses, and contamination from dirt and body fluids wherein remaining live microorganisms not in intimate contact with the surface are readily washed away due to the hydrophobic and oleophobic nature of the surface created by the electron deficient surface and the unavailability of nutrients in the siloxane coating and the tight polymer with sub-nanometer molecules that does not allow micro-organisms or their protein elaborates to gain grasp of the surface by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

IV. A method for self sterilization of surfaces and providing a biostatic or biocidal surface that is remediable present in hospitals including but not limited to medical equipment, beds, floors, walls, ceilings, bathrooms, operating rooms, operating room equipment, ventilation ducts and HVAC air handling equipment, tile, cement, terrazzo, curtains, carpet, brushed or polished stainless steel, painted, wall paper, vinyl, leather, and plastics by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

V. A method for self sterilization and providing a biostatic or biocidal surface that is remediable of ambulances, police vehicles, fire fighting vehicles, first responder vehicles and other emergency medical vehicles including but not limited to beds, seats, control or instrument panels, dashboards, side or “kick panels”, trim, steering wheels, metal, plastic or synthetic compound parts, control knobs, radios, shift or other levers, door handles, arm rests, carpet, rubber mats, gurneys, cabinets, metal floors, synthetic flooring, medical equipment, handles, and pressure bottles in such vehicles by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

VI. A method of providing and self-decontamination and remediation through easy cleaning of bio-warfare agents and residues on cities and military vehicles and fighting platforms of all types to include both germ and toxic organic and inorganic compounds from all surfaces inside and outside of buildings, sidewalks, roads, fences, signage, utility structures, record and archival storage, construction materials, decorative materials, infrastructure, and contents of buildings including but not limited to metal, plastic or synthetic compound parts, concrete, composites of concrete, asphalt, carpet, leather, fabric, cabinets, metal floors, synthetic flooring, wood, wood flooring, storage equipment, utility cabinets and distribution, HVAC systems, and pressure vessels by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

VII. A method of rendering any type of surfaces resistant to mold, also easily cleaned of mold, hydrophobic, oleophobic, and promoting cleaning without harsh soaps or detergents by coating same with oligomeric siloxanes, applied as catalyzed or partially catalyzed reactive silanols, to create a net positive surface charge on the coating to affect the stated properties.

VIII. A method of immunizing buildings, facilities, and equipment contained therein from the immediate effects and to allow rapid decontamination and remediation from exposure to biological warfare agents, chemical warfare agents, and radiological warfare agents by coating same as an overcoat to other coatings, or directly over uncoated materials or fabrics with oligomeric siloxanes, applied as catalyzed or partially catalyzed reactive silanol, to create a net positive surface charge on the coating to effect the stated properties.

IX. A method for cleaning and pre-treating such surfaces to achieve a functional antimicrobial surface, an aesthetically pleasing surface, or both for by coating same with oligomeric siloxanes, applied as catalyzed or partially catalyzed reactive silanol, to create a net positive surface charge on the coating to affect the stated properties.

X. A method of rendering surfaces contaminated with fine, potentially or actually hazardous particulates such as, but not limited to, mold spores, asbestos, bacteria, viruses, protozoa, or biological warfare agents safe to handle or scrap by encapsulating the particulates in a film of oligomeric siloxanes, applied as catalyzed or partially catalyzed reactive silanol, to create a net positive surface charge on the coating to effect the stated properties.

XI. A method of providing a positively charged, electron deficient, surface by coating surfaces with oligomeric siloxanes and associated formulations, for the patents cited above, to effect self sterilizing and anti-microbial qualities including the use of organo-siloxanes and silanes that may not exhibit as robust properties for reasons cited herein.

XII. A method of forming a thin coating of interpenetrating polysiloxane with organic moieties predominantly oriented toward the exposed surface of said coating to produce a permanent positive surface potential of said coating onto a substrate rendering the surface bio-static, self-sterilizing, or remediable, said coating comprising a reactive silanol, that is, an aqueous or non-aqueous dispersion of the partial condensate of monomethyl or monethyl silanol (by hydrolysis of monomethyl or monethyl alkoxysilane) alone or in admixture with minor amounts of other silanols, e.g., gamma-glycidyloxy silanol, phenyl silanol, etc, wherein the dispersions contain divalent metal cations, e.g., $Ca^{+2}$, alcohol or water dispersants, and which may optionally contain film-enhancing additives such as, but not limited to, hydrolysis catalysts like acetic acid, ethylene glycol ether co-solvents, silicates or hydrolyzed silicates, solid or water-soluble pigments, gellation inhibitors like chromium acetate hydroxides, or metal alcholates of the of formula (2):

$$M(OR^{+3})_m \qquad (2)$$

where M is a metal valence 2, 3 or 4, or mixture of two or more such metals;

R represents a lower alkyl group; and, m represents a number or 2, 3 or 4;

XIII. A method of forming a thin coating of siloxane with organic moieties predominantly oriented toward the exposed surface of said coating to produce a positive surface potential of said coating onto a substrate rendering the surface bio-static, self-sterilizing, or remediable, said coating comprising a pre-catalyzed reactive silanol, that is, an aqueous or non-aqueous dispersion of the partial condensate of monomethyl or monethyl silanol (by hydrolysis of monomethyl or monethyl alkoxysilane) alone or in admixture with minor amounts of other silanols, e.g., gamma-glycidyloxy silanol, phenyl silanol, etc, wherein the dispersions contain divalent metal cations, e.g., $Ca.^{+2}$, in an alcohol dispersant, and which may optionally contain film-enhancing additives such as, but not limited to, hydrolysis catalysts, silicates or hydrolyzed silicates, solid or water-soluble pigments, gellation inhibitors like chromium acetate hydroxides, or metal alcholates of the of formula (2):

$$M(OR^3)_m \qquad (2)$$

where M is a metal valence 2, 3 or 4, or mixture of two or more such metals;

R represents a lower alkyl group; and, m represents a number or 2, 3 or 4;

XIV. A method of forming a thin, hard coating of polysiloxane with organic moieties predominantly oriented toward the exposed surface of said coating to produce a positive surface potential of said coating onto a substrate rendering the surface bio-static, self-sterilizing, or remediable, said coating comprising a reactive silanol composition as in paragraph XIII, further comprising a hardener composed of water, acidified water preferably acidified with acetic acid, or water or acidified water and minor additions of additives such as epoxy or amino silanes applied by mechanical polishing to form and cure said siloxane at ambient temperatures whereby a hard, low porosity interpenetrating network of organosolixanes with organic moieties oriented toward the surface is formed on the substrate.

XV. A dense siloxane coating composition formed onto a substrate wherein organic moieties of said coating are oriented toward the exposed surface thereof causing a permanent positively charged surface potential rendering the surface bio-static, self-sterilizing, or remediable comprising a reactive silanol, that is, an aqueous or non-aqueous dispersion of the partial condensate of monomethyl or monethyl silanol (by hydrolysis of monomethyl or monethyl alkoxysilane) alone or in admixture with minor amounts of other silanols, e.g., gamma-glycidyloxy silanol, phenyl silanol, etc, wherein the dispersions contain divalent metal cations, e.g., $Ca^{+2}$, alcohol or water dispersants, and which may optionally contain film-enhancing additives such as, but not limited to, hydrolysis catalysts like acetic acid, ethylene glycol ether co-solvents, silicates or hydrolyzed silicates, solid or water-soluble pigments, gellation inhibitors like chromium acetate hydroxides, or metal alcholates of the of formula (2):

$$M(OR^3)_m \qquad (2)$$

where M is a metal valence 2, 3 or 4, or mixture of two or more such metals;

R represents a lower alkyl group; and, m represents a number or 2, 3 or 4;

XVI. A siloxane coating composition formed onto a substrate wherein organic moieties of said coating are oriented toward the exposed surface thereof causing a positively charged surface potential rendering the surface bio-static, self-sterilizing, or remediable comprising a pre-catalyzed reactive silanol, that is, an aqueous or non-aqueous dispersion of the partial condensate of monomethyl or monethyl silanol (by hydrolysis of monomethyl or monethyl alkoxysilane) alone or in admixture with minor amounts of other silanols, e.g., gamma-glycidyloxy silanol, phenyl silanol, etc, wherein the dispersions contain divalent metal cations, e.g., $Ca^{+2}$, in an alcohol dispersant, and which may optionally contain film-enhancing additives such as, but not limited to, hydrolysis catalysts, silicates or hydrolyzed silicates, solid or water-soluble pigments, gellation inhibitors like chromium acetate hydroxides, or metal alcholates of the of formula (2):

$$M(OR^3)_m \qquad (2)$$

where M is a metal valence 2, 3 or 4, or mixture of two or more such metals;

R represents a lower alkyl group; and, m represents a number or 2, 3 or 4;

XVII. A polysiloxane coating composition formed onto a substrate wherein organic moieties of said coating are oriented toward the exposed surface thereof causing a positively charged surface potential rendering the surface bio-static, self-sterilizing, or remediable comprising a reactive silanol composition as in paragraph XVI, further comprising a hardener composed of water, acidified water preferably acidified with acetic acid, or water or acidified water and minor additions of additives such as epoxy or amino silanes applied by mechanical polishing to form and cure said siloxane at ambient temperatures whereby a hard, low porosity interpenetrating network of organosolixanes with organic moieties oriented toward the surface is formed on the substrate.

DETAILED DESCRIPTION OF THE INVENTION

While not wishing to be bound by formulae provided for information, this invention is based on the discovery that reactive silanol compositions such as those described in the referenced Schutt et. al. patents when catalyzed or partially catalyzed and applied to the methods described herein cure into a dense, siloxane film where organic moieties are oriented toward the surface of the film causing a permanent, positive surface potential. The silicon atoms in the siloxane coating matrix strongly attract electrons, while the surface organic groups easily give up electrons. This phenomenon allows the electron cloud to skew downward, affecting an electron deficient surface that has a net positive charge for the life of the coating. The coating of any of the aforementioned and virtually any surface allows this unique property to form. Positive surface charge effects can be seen in multi-part and catalyzed and partially catalyzed one part siloxane coatings and are envisioned herein as part of the invention.

Siloxane coatings are also very resistant to micro-organisms because of the very tight silica oxygen polymer formed, with the small sub-nanometer sized molecules, with the positive charged surface. Surfaces treated with reactive silanols to the methods described herein are not only anti-microbial, but can be made sterile or the microbe population can be reduced to below the Minimal Infection Concentration (MIC) with no cleaning, minimal cleaning with simple soap and water instead of disinfectants or harsh chemicals, or can be decontaminated with harsh chemicals or disinfectants and no scrubbing without damaging the treated surfaces. Treating porous materials such as grout and concrete can render such surfaces impervious to staining and contamination from fine, hazardous particulates or fluids. Exhibit A is a scan of a report from a laboratory running the ASTM G-21 test for mold spores showing a perfect rating for lack of spores on a sample coated with a catalyzed siloxane coating against a control.

A simplified model in accordance with the present invention is shown below:

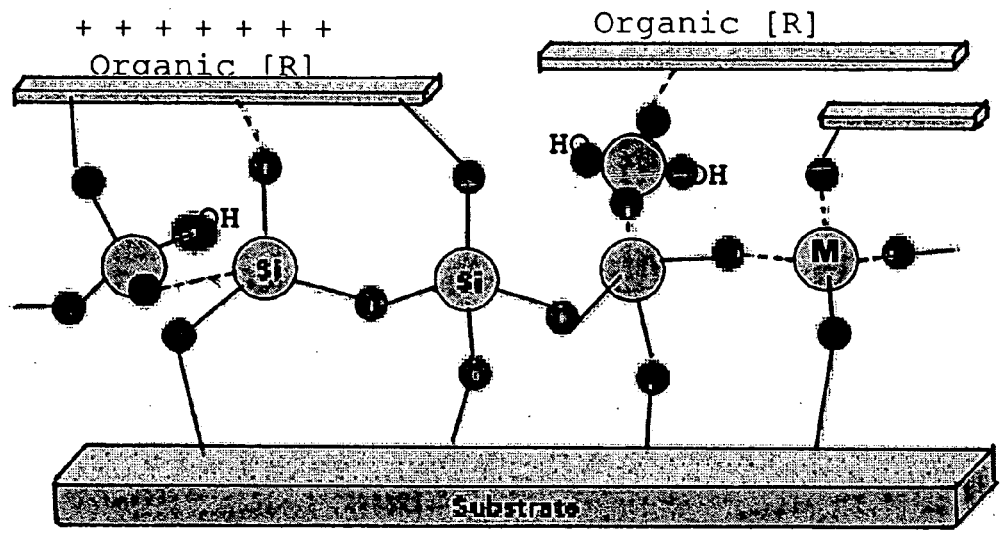

This simplified model of cured siloxane applied as a reactive silanol illustrating organic groups oriented at the surface of an interpenetrating network of siloxane covalently bonded to the substrate.

Oligomeric Siloxane coatings can be of two basic types. The first are the type of siloxane that is a multi-part catalyzed system as cited in the patents referenced or an organo-silane catalyzed in a similar manner. The second is a partially catalyzed siloxane coating where moisture is absorbed from the air or artificial means to complete hydrolysis of component silanes upon application; or a partially catalyzed siloxane where in silane hydrolyzation into silanols is interrupted by diluting with 50-90% by weight solvent. The partially hydrolyzed reactive silanol exhibits very low molecular weight silanols which can be applied to a surface by spray or wipe. After one to five minutes to allow the silanols to bond with the surface and to allow most of the solvent to solve off, a catalyzing or curing agent such as dilute acetic acid in water is used to supply moisture for hydrolysis, polycondesation, and siloxane formation into a more robust film to form a very thin coating that is not as durable as a multi-part catalyzed coating, but can be easily applied by untrained consumers or maintenance personnel as a single or two-part system, usually in a simple spray bottle.

Such coatings applied to any of the surfaces stated, will provide an electron deficient surface, in effect, a positively charged surface, that will not provide a media for multiplication of viruses and bacteria, and will through their structure of small molecules and hydrophobic and oleophobic surfaces provide an ease of cleaning of residues for a decontamination process.

Organo-siloxanes and silanes are also envisioned under this invention; however, they do not exhibit the compact structure that oligomeric siloxanes applied as reactive silanol sols exhibit due to molecule size, stability, and durability and would be deficient in the cleaning ability as they would be more susceptible to penetration and adherence of microbial growth, and would also may be less polar on their surface displaying less positive surface charge. Also, if organo compounds such as polyls or large ($C_{16}$ or greater) organosilanes are used that may exhibit equal or greater surface charge, the permanence of the surface would be greatly reduced.

The invention will now be illustrated by the following non-limiting examples. It is understood that these examples are given by way of illustration only and without intent to limit the invention thereto.

EXAMPLE 1

Ambulance Patient Transport Cabs

In Houston, the interiors of the patient transport cabs of four ambulances were cleaned by standard methods employed by the ambulance company, inspected and secondarily cleaned and dried as necessary to promote adhesion and formation of a thin oligomeric siloxane film. For each ambulance, 3-part reactive silanol was vigorously mixed in an open pot in a high bay with adequate ventilation and inducted for thirty minutes. The mixtures was applied by spray to all interior surfaces and appurtenances of the cab and touched up with disposable foam brushes to remove drips, prevent pooling, and blend in holidays. The film was cured in open air for 48 hours before putting the ambulances back into service. Ambulance operators reported that cleaning and disinfection time between runs was reduced from 45 minutes to one hour before the reactive silanol treatment to an average of 15 minutes after treatment.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. A method of forming a thin coating of interpenetrating polysiloxane with organic moieties predominantly oriented toward the exposed surface of said coating to produce a permanent positive surface potential of said coating onto a substrate rendering the surface bio-static, self-sterilizing, or remediable, said method comprising the steps of:
   A. providing a reactive silanol as an aqueous or non-aqueous dispersion of a partial condensate of monomethyl or monethyl silanol by hydrolyzing monomethyl or monethyl alkoxysilane;
   B. dispersing said reactive silanol in an alcohol or water or both to form an admixture;
   C. applying said admixture to the substrate;
   D. allowing said admixture to cure and harden into an interpenetrating polysiloxane with organic moieties predominantly oriented toward said exposed surface forming a permanent positive surface potential of said coating to produce the bio-static, self-sterilizing and remediable said exposed surface; and
   E. further curing said coating by applying a hardener composed of water or acidified water and epoxy or amino silanes, said hardener being applied by mechanical polishing at ambient temperatures wherein a hard, low porosity interpenetrating network of organosolixanes with organic moieties oriented toward the surface is formed atop the substrate.

2. The method as set forth in claim 1, further comprising:
F. adding one or more silanes with said admixture provided in Step A, said silane including gama-glycidyloxy silane, amino silane, keto silane, or phenyl silane.

3. The method as set forth in claim 1, further comprising:
F. mixing a divalent metal cation with said admixture after Step A.

4. The method as set forth in claim 1, further comprising:
F. acidifying water with acetic acid, boric acid or phosphoric acid in conjunction with Step B.

5. The method as set forth in claim 4, further comprising:
G. adding one or more silanes with said admixture provided in Step A, said silane including gama-glycidyloxy silane, amino silane, keto silane, or phenyl silane.

6. The method as set forth in claim 4, further comprising:
G. mixing one or more film enhancing additives with said admixture in Step B;
said film enhancing additives including (I) hydrolysis catalysts including acetic or boric acid, (ii) co-solvents including ethylene or propylene glycol ethers, (iii) silicates or hydrolyzed silicates, (iv) solid or water soluble pigments, (v) siloxane surfactants, (vi) siloxane defoamers, or (vii) gellation inhibitors of the formula:

$$M(OR^3)_m \qquad (2)$$

where M is a metal valence 2, 3 or 4, or mixture of two or more such metals;
R represents a lower alkyl group; and,
m represents a number or 2, 3 or 4.

7. The method as set forth in claim 6, further comprising:
H. adding one or more silanes with said admixture provided in Step A, said silane including gama-glycidyloxy silane, amino silane, keto silane, or phenyl silane.

8. The method as set forth in claim 4, further comprising:
G. mixing a divalent metal cation with said admixture after Step A.

9. The method as set forth in claim 8, further comprising:
H. adding one or more silanes with said admixture provided in Step A, said silane including gama-glycidyloxy silane, amino silane, keto silane, or phenyl silane.

10. The method as set forth in claim 9, further comprising:
I. mixing one or more film enhancing additives with said admixture in Step B;
said film enhancing additives including (i) hydrolysis catalysts including acetic or boric acid, (ii) co-solvents including ethylene or propylene glycol ethers, (iii) silicates or hydrolyzed silicates, (iv) solid or water soluble pigments, (v) siloxane surfactants, (vi) siloxane defoamers, or (vii) gellation inhibitors of the formula:

$$M(OR^3)_m \quad (2)$$

where M is a metal valence 2, 3 or 4, or mixture of two or more such metals;
R represents a lower alkyl group; and,
m represents a number or 2, 3 or 4.

11. The method as set forth in claim 1, further comprising:
F. mixing one or more film enhancing additives with said admixture in Step B;
said film enhancing additives including (i) hydrolysis catalysts including acetic or boric acid, (ii) co-solvents including ethylene or propylene glycol ethers, (iii) silicates or hydrolyzed silicates, (iv) solid or water soluble pigments, (v) siloxane surfactants, (vi) siloxane defoamers, or (vii) gellation inhibitors of the formula:

$$M(OR^3)_m \quad (2)$$

where M is a metal valence 2, 3 or 4, or mixture of two or more such metals;
R represents a lower alkyl group; and,
m represents a number or 2, 3 or 4.

12. The method as set forth in claim 11, further comprising:
G. mixing a divalent metal cation with said admixture after Step A.

13. The method as set forth in claim 12 further comprising:
H. adding one or more silanes with said admixture provided in Step A, said silane including gama-glycidyloxy silane, amino silane, keto silane, or phenyl silane.

14. A siloxane coating formed onto a substrate wherein organic moieties of said coating are predominantly oriented toward the exposed surface of said coating to produce a permanent positive surface potential on the surface of said coating rendering the surface bio-static, self-sterilizing and/or remediable, said coating being derived from curing an admixture comprising:
a reactive silanol as an aqueous or non-aqueous dispersion of a partial condensate of monomethyl or monethyl silanol formed by hydrolyzing monomethyl or monethyl alkoxysilane and wherein said silanol is dispersed in alcohol or water or both to form an admixture;
said exposed surface of said coating forming a permanent positive surface potential to produce the bio-static, self-sterilizing and/or remediable said exposed surface; and
a hardener including water or acidified water and epoxy or amino silanes, said hardener applied by mechanical polishing to further cure said coating at ambient temperatures wherein a hard, low porosity interpenetrating network of organosolixanes with organic moieties oriented toward the surface is formed atop the substrate.

15. A siloxane coating as set forth in claim 14, further comprising:
one or more silanes with said admixture, said silane including gama-glycidyloxy silane, amino silane, keto silane, or phenyl silane.

16. A siloxane coating as set forth in claim 14, further comprising:
a divalent metal cation including $Ca^{+2}$ admixed with said admixture.

17. A siloxane coating as set forth in claim 14, said admixture further comprising:
water acidified with acetic acid, boric acid or phosphoric acid.

18. A siloxane coating as set forth in claim 17, further comprising:
one or more silanes with said admixture, said silane including gama-glycidyloxy silane, amino silane, keto silane, or phenyl silane.

19. A siloxane coating as set forth in claim 17, further comprising:
a divalent metal cation including $Ca^{+2}$ admixed with said admixture.

20. A siloxane coating as set forth in claim 19, further comprising:
one or more silanes with said admixture, said silane including gama-glycidyloxy silane, amino silane, keto silane, or phenyl silane.

21. A silanol coating as set forth in claim 20, said admixture further comprising:
one or more film enhancing additives; said film enhancing additives including (I) hydrolysis catalysts including acetic or boric acid, (ii) co-solvents including ethylene or propylene glycol ethers, (iii) silicates or hydrolyzed silicates, (iv) solid or water soluble pigments, (v) siloxane surfactants, (vi) siloxane defoamers, or (vii) gellation inhibitors of the formula:

$$M(OR^3)_m \quad (2)$$

where M is a metal valence 2, 3 or 4, or mixture of two or more such metals;
R represents a rower alkyl group; and,
m represents a number or 2, 3 or 4.

22. A silanol coating as set forth in claim 14, said admixture further comprising:
one or more film enhancing additives;
said film enhancing additives including (i) hydrolysis catalysts including acetic or boric acid, (ii) co-solvents including ethylene or propylene glycol ethers, (iii) silicates or hydrolyzed silicates, (iv) solid or water soluble pigments, (v) siloxane surfactants, (vi) siloxane defoamers, or (vii) gellation inhibitors of the formula:

$$M(OR^3)_m \quad (2)$$

where M is a metal valence 2, 3 or 4, or mixture of two or more such metals;
R represents a lower alkyl group; and,
m represents a number or 2, 3 or 4.

23. A siloxane coating as set forth in claim 22, further comprising:
a divalent metal cation including $Ca^{+2}$ admixed with said admixture.

24. A siloxane coating as set forth in claim 23, further comprising:

one or more silanes with said admixture, said silane including gama-glycidyloxy silane, amino silane, keto silane, or phenyl silane.

25. A silanol coating as set forth in claim 14, said admixture further comprising:

one or more film enhancing additives; said film enhancing additives including (I) hydrolysis catalysts including acetic or boric acid, (ii) co-solvents including ethylene or propylene glycol ethers, (iii) silicates or hydrolyzed silicates, (iv) solid or water soluble pigments, (v) siloxane surfactants, (vi) siloxane defoamers, or (vii) gellation inhibitors of the formula:

$$M(OR^3)_m \qquad (2)$$

where M is a metal valence 2, 3 or 4, or mixture of two or more such metals;

R represents a lower alkyl group; and, m represents a number or 2, 3 or 4.

26. A siloxane coating as set forth in claim 25, further comprising:

one or more silanes with said admixture, said silane including game-glycidyloxy silane, amino silane, keto silane, or phenyl silane.

* * * * *